| United States Patent [19]
Winston et al. | [11] Patent Number: 4,812,308 |
| --- | --- |
| | [45] Date of Patent: Mar. 14, 1989 |

[54] HYDROGEN PEROXIDE-RELEASING TOOTH POWDER

[75] Inventors: Anthony Winston, East Brunswick; Herman Marder, Red Bank; Wayne Sorenson, Belle Mead, all of N.J.

[73] Assignee: Church & Dwight Co., Inc., Princeton, N.J.

[21] Appl. No.: 17,143

[22] Filed: Feb. 20, 1987

[51] Int. Cl.$^4$ .................. A61K 7/16; A61K 7/18; A61K 9/20

[52] U.S. Cl. .................. 424/52; 424/49; 424/53

[58] Field of Search .................. 424/49, 52, 53

[56] References Cited

U.S. PATENT DOCUMENTS

| | | | |
| --- | --- | --- | --- |
| 802,099 | 10/1905 | Gane | 424/53 |
| 808,105 | 12/1905 | Morse | 424/53 |
| 2,071,043 | 2/1937 | Nitardy | 424/53 |
| 2,120,430 | 6/1938 | Rieche et al. | 424/53 |
| 2,170,052 | 8/1939 | Heim et al. | 424/53 |
| 2,275,979 | 3/1942 | Molnar | 424/53 |
| 3,885,028 | 5/1975 | Cella et al. | 424/52 |
| 3,937,804 | 2/1976 | Delaney et al. | 424/52 |
| 4,226,851 | 10/1980 | Sompayrac | 424/53 |
| 4,273,759 | 6/1981 | Gaffar et al. | 424/54 |
| 4,302,441 | 11/1981 | Muhlemann et al. | 424/48 |
| 4,350,681 | 9/1982 | Fulton, Jr. | 424/53 |
| 4,431,631 | 2/1984 | Clipper et al. | 424/53 |
| 4,476,108 | 10/1984 | Kessler et al. | 424/50 |
| 4,522,805 | 6/1985 | Gordon | 424/52 |
| 4,528,180 | 7/1985 | Schaeffer | 424/52 |
| 4,537,764 | 8/1985 | Pellico et al. | 424/50 |
| 4,537,765 | 8/1985 | Gaffar et al. | 424/53 |
| 4,537,778 | 8/1985 | Clipper et al. | 424/53 |
| 4,582,701 | 4/1986 | Piechota | 424/52 |
| 4,647,451 | 3/1987 | Piechota | 424/52 |

OTHER PUBLICATIONS

Rosling, et al.; Journal of Clinical Periodontology, vol. 10, pp. 487-514, 1983.

Keyes P. H. et al., Quintessence International No. 1, Jan. 1978, report 1590, pp. 51-56 and 69-75.

Balsam M. S. et al., Cosmetics: Science and Technology, vol. 1, 2nd Edition, Wiley Interscience (1972) p. 496.

*Primary Examiner*—Shep K. Rose
*Attorney, Agent, or Firm*—Bryan, Cave, McPheeters & McRoberts

[57] ABSTRACT

A stable, palatable and safe hydrogen peroxide releasing tooth powder composition containing sodium bicarbonate and sodium percarbonate in combination with flavoring agents, sweeteners, fluoridating agents, additional abrasives, surfactants and/or additional adjuvants.

20 Claims, No Drawings

HYDROGEN PEROXIDE-RELEASING TOOTH POWDER

TECHNICAL FIELD

This invention relates to a stable, palatable hydrogen peroxide-releasing tooth powder.

BACKGROUND OF THE INVENTION

Periodontal disease afflicts over an estimated 90 percent of the world's population. Lassari, E.P., *Dental Biochemistry*, 191-3, (1976). Although this disease is not life threatening, it often results in serious discomfort and tooth loss. The basic cause of this disease is bacteriological in nature. Both topical and systemic bactericidal agents have been found effective in combating the disease. *Biological Basis of Periodontal Maintenance Therapy*, G.C. Armitage, Proxis Publishing Company, 1980, pages 34-78.

Recently, it has been demonstrated that combinations of various salts and hydrogen peroxide solution, when properly applied as part of a treatment under the supervision of a dentist, are effective in controlling periodontitis. B.G. Rosling et al, Journal of Clinical Periodontology, Vol. 10 pp 487-514, 1983. Sodium bicarbonate, a particularly convenient and palatable non-toxic salt, is believed to be effective in this treatment. Keyes P.H. et al, Quintessence International No. 1, January 1978, Report 1590, pages 51-56 and No. 2 February 1978, pages 69-75.

The bacteria causing periodontal disease are anaerobic. Armitage, G.C., Biological Basis of Periodontal Maintenance Therapy, 1980. By providing high levels of oxygen, hydrogen peroxide is believed to be effective in killing these bacterial organisms. Hydrogen peroxide is the preferred oxidizing agent as it is readily available, proven effective and non-toxic.

In addition to treating periodontal disease, many individuals like to use baking soda and peroxide to clean their teeth. Several of the benefits cited by those using this combination include ability to remove stains, a clean feeling in the mouth, less mouth odor, and healthy gums.

A mixture of an approximately 60 percent sodium bicarbonate paste with a 3 percent solution of hydrogen peroxide has been used to treat periodontal disease. This method requires the user, immediately before use, to prepare the mixture in the palm of the hand. The mixture is then applied along the gum line. Due to the foaming action of the hydrogen peroxide, and because the mixture is prepared on the palm of the hand, this procedure is messy.

To overcome the inconvenience of the above procedure, various dentifrices have been formulated which contain oxidizing agents such as sodium perborate (Cella, et al., U.S. Pat. No. 3,885,028 and Molnar, U.S. Pat. No. 2,275,979), potassium chlorate, urea peroxide (Gordon, U.S. Pat. No. 4,522,805 and Schaeffer, U.S. Pat. No. 4,528,180) and magnesium peroxide. Balsam, M.S. et al, Cosmetics: Science and Technology, Volume 1, Second Edition, Wiley Interscience (1972) page 496.

Sodium perborate and potassium chlorate do not release significant levels of hydrogen peroxide in water. Kirk-Othmer Encyclopedia of Chemical Technology, Third Edition, Volume 17, page 1-22; Kern, D.M., J. Am. Chem. Soc. 77 5458, 1955. Although sodium perborate has been classified category 1 (Federal Register, Oct. 7, 1982) for temporary use as an oral wound cleaner, it is of questionable safety for frequent topical use on the mucous membranes of the mouth and throat because it contains boron which can undergo systemic absorption. (Federal Register Vol. 44 No. 214 page 63282, Friday, Nov. 2, 1979, Proposed Rules). Sodium perborate also has an undesirably low solubility in water of about 2.5%. This low solubility limits the concentration of oxidizing agent. Magnesium peroxide, an essentially insoluble salt in water, is similarly undesirable. Handbook of Chemistry and Physics, 59th Edition, 1978-79.

Various peroxide-releasing dentifrice formulations utilize urea peroxide as the oxidizing agent. However, urea peroxide in combination with sodium bicarbonate is not stable. As a result, preparations have been proposed in which the urea peroxide and sodium bicarbonate components are in separate compartments of a container (see Schaeffer, U.S. Pat. No. 4,528,180, column 2, lines 4-9).

Other sodium bicarbonate-containing, peroxide-releasing dentifrices may incorporate enzymes for generating hydrogen peroxide in situ. (See Kessler et al., U.S. Pat. No. 4,476,108 and Pellico et al., U.S. Pat. No. 4,537,764). However, the formation of hydrogen peroxide by enzymes is so slow that only low levels of peroxide are produced during brushing with these dentifrices.

Alkali and alkaline earth metal percarbonates, e.g., ammonium percarbonate, were also described as peroxide-releasing reagents for dentifrices more than eighty years ago. (Gane, U.S. Pat. No. 802,099 granted Oct. 17, 1905.) The percarbonates have not been actually used in dentifrice formulations, however, because of their high pH in solution which could cause severe irritation of the gums. Dentifrices containing such a percarbonate and an alkali metal bicarbonate have not been previously described or used.

It is among the objects of the present invention to provide a stable, peroxide-releasing tooth powder. It is a further object of the invention to provide such a formulation which is useful in the treatment of periodontal disease and which minimizes dental caries, in a safe, more convenient and more palatable form than embodied in any prior art formulation of which we are aware.

SUMMARY OF THE INVENTION

In accordance with the present invention, a tooth powder is provided comprising a least 40% by weight of a mixture of sodium bicarbonate and sodium percarbonate which, on contact with water, rapidly releases between 0.5 to 5% active hydrogen peroxide by weight of the finished product. Tooth powders prepared in accordance with this invention provide a convenient method of supplying a premixed stable combination of sodium bicarbonate and percarbonate, in a palatable form.

Thus, we have found that tooth powders containing a sodium bicarbonate abrasive mixed with sodium percarbonate, the bicarbonate desirably being incorporated in amounts of from about 40 to 98% by weight of the powder, and either with or without other dentifrice adjuvants such as fluoride (e.g., sodium fluoride), sweetener (e.g., saccharin), flavorant, etc., are quite palatable and surprisingly stable with regard to loss of oxygen, as compared with dentifrices prepared from other bicarbonate, hydrogen peroxide-releasing formulations, e.g., those containing urea peroxide. Further-more, the tooth powder formulation hereof incorporates the relatively inexpensive hydrogen peroxide-releasing agent, sodium percarbonate, in a quite safe and palatable form. As indicated above, sodium percarbonate cannot normally be utilized in the oral cavity because it has an excessively high pH in solution which could cause severe irritation of the gums. The presence of sodium bicarbonate in admixture therewith in a powder formulation, serves to reduce the pH and provide a safe and palatable dentifrice.

In addition to the preceding advantages, the product of the present invention—containing the combination of the two named ingredients—is more convenient to use, and less messy than previous formulas which the user had to mix immediately before use. Moreover, the dosage ratios of the two ingredients may be accurately controlled.

DETAILED DESCRIPTION

The tooth powder of the invention preferably contains other ingredients in addition to sodium bicarbonate and sodium percarbonate. Such ingredients may include flavoring agents, sweeteners, fluoridating agents, additional abrasives, surfactants, flow aids and/or additional adjuvants, as well recognized by those skilled in the art.

Examples of suitable flavoring agents include the flavoring oils, for example, oils of spearmint, peppermint, wintergreen, sassafras, clove, sage, eucalyptus, marjoram, cinnamon, lemon and orange, as well as sodium methylsalicylate. The flavoring agent may be present in the tooth powder in an amount up to about 3% by weight of the tooth powder, preferably within the range of from about 0.05% to 3%.

Suitable sweeteners may also be included in the tooth powders of the present invention. Suitable sweeteners include lactose, maltose, sorbitol, aspartame, and saccharin. The amount of sweetener present in the tooth powder is desirably within the range of from about 0.20% to 3.0%. The flavoring and sweetening agents make the tooth powder more palatable.

The tooth powder may additionally contain a fluoridating agent for the prevention of dental caries. Included among known fluoridating agents suitable for use herein are sodium, potassium, ammonium, lithium and amine fluorides, monofluorophosphate salts such as sodium, potassium, ammonium and lithium monofluorophosphate, and other fluoridating agents well known to those skilled in the art. The fluoridating agents are present in an effective but non-toxic amount, e.g., in amounts of up to about 2% by weight of the tooth powder. Preferably, the composition contains approximately 1000 ppm fluoride, either in the form of a fluoride or monofluorophosphate salt. This level may be provided by 0.22% sodium fluoride or 0.76% sodium monofluorophosphate.

The tooth powder may also contain from about 1 to 50% by weight of an additional abrasive material. Abrasive materials suitable as additional abrasives in the tooth powders are well known in the art and include calcium carbonate, e.g., chalk, dicalcium phosphate, silica, alumina, titanium dioxide, zirconium silicate, and the like, or mixtures thereof.

Suitable surfactants which may be incorporated in the tooth powder include, for example, water-soluble salts of the higher alkyl sulfates, such as sodium lauryl sulfate; water-soluble salts of sulfonated monoglycerides of fatty acids, such as sodium coconut monoglyceride sulfonate; salts of amides of higher fatty acids with lower aliphatic amino acids, such as sodium lauryl sarcosinate, and the like. The surfactant may be present in the tooth powder in amounts ranging up to about 2% by weight.

A flow aid is also included in the tooth powder of the present invention. Suitable flow aids include magnesium oxide, fumed silica, precipitated anhydrous silica, diatomaceous earth, sodium aluminosilicate, magnesium silicate, calcium aluminosilicate, and tricalcium phosphate. The flow aid is incorporated in the tooth powder in an amount of up to about 1% by weight of the toothpowder, preferably in an amount within the range of from about 0.1 to 0.2% by weight thereof.

In a preferred form, the tooth powder of the present invention comprises from about 40 to 100% by weight of the mixture of sodium bicarbonate and sodium percarbonate, desirably in proportions such that the total formulation contains from about 48 to 98% by weight bicarbonate and from about 1 to 12% by weight percarbonate; about 0.2–3% by weight of a flavoring agent; about 0.1–5% by weight of a sweetener; and from about 0.2 to 2.0% by weight of a fluoridating agent. The bicarbonate particles are preferably provided in the size distributions described in Winston et al., U.S. Pat. No. 4,547,362 granted Oct. 15, 1985, the disclosure of which is incorporated by this reference herein; desirably, the particles thus possess a median particle size of about 74–210 microns, most desirably about 74 to 149 microns.

The following examples, in which all parts and percentages are given by weight, illustrate the method and composition of the present invention. The examples are given for purposes of illustration only and should not be construed to limit the spirit or scope of the invention.

EXAMPLES 1–4

Tests were run to compare the stability of toohpowders containing the sodium percarbonate/sodium bicarbonate tooth powder formulations of the invention, in the presence or absence of other dentifrice ingredients, with corresponding sodium bicarbonate/hydrogen peroxide dentifrice formulations.

The results are shown in Tables I and II.

TABLE I

Compositions of Bicarbonate/Percarbonate Tooth Powders Of The Invention Stability Results

|  | Examples | | | |
| --- | --- | --- | --- | --- |
|  | 1 | 2 | 3 | 4 |
| Sodium Percarbonate | 6.0 | 6.0 | 2.0 | 2.0 |
| Sodium Bicarbonate | 94.0 | 90.41 | 98.0 | 94.25 |
| Sodium Fluoride | — | 0.21 | — | 0.22 |
| Spray Dried Flavor | — | 1.88 | — | 1.96 |
| Sodium Saccharin | — | 1.41 | — | 1.47 |
| Magnesium Oxide | — | 0.09 | — | 0.1 |
|  | 100.0 | 100.0 | 100.0 | 100.0 |
|  | Controls | | | |
|  | A | B | C | D |
| Sodium Bicarbonate | 60.6 | 58.29 | 82.2 | 79.07 |
| Sodium Fluoride | — | 0.13 | — | .18 |
| Spray Dried Flavor | — | 1.21 | — | 1.64 |
| Sodium Saccharin | — | 0.91 | — | 1.23 |
| Magnesium Oxide | — | 0.06 | — | 0.08 |
| Hydrogen Peroxide (3% solution) | 39.4 | 39.4 | 17.8 | 17.8 |
|  | 100.0 | 100.00 | 100.0 | 100.0 |

The level of active oxygen released by each of the above formulations was determined as follows:

1-2g of each sample was accurately weighed and dissolved in 75-100 mls of distilled water. 10 mls of 3M sulfuric acid were gradually added and the solution titrated with 0.1N KMnO$_4$ solution.

$$\% O_2 = \frac{\text{mls KMnO}_4 \times N(\text{normality}) \times 0.8}{\text{Sample wt}}$$

The portions of the respective samples were exposed to varying atmospheric conditions, and their active oxygen contents thereafter determined, as indicated above. The results are set forth in the following tabulations:

TABLE II

Peroxide-Releasing Characteristics Of Tooth Powders Of The Invention
% Active Oxygen

| | Examples | | | | Controls | | | |
|---|---|---|---|---|---|---|---|---|
| | 1 | 2 | 3 | 4 | A | B | C | D |
| Initial Content | 0.64 | 0.65 | 0.22 | 0.24 | 0.54 | 0.48 | 0.27 | 0.23 |
| 1 Week Ambient (70° F.) | 0.64 | 0.65 | 0.19 | 0.17 | 0 | 0 | 0 | 0 |
| 2 Months Ambient (70° F.) | 0.66 | 0.58 | 0.24 | 0.18 | 0 | 0 | 0 | 0 |
| 1 Week 80° F./80% RH | 0.63 | 0.63 | 0.23 | 0.16 | 0 | 0 | 0 | 0 |
| 2 Months 80° F./80% RH | 0.54 | 0.65 | 0.17 | 0.18 | 0 | 0 | 0 | 0 |
| 1 Week 104° F. | 0.67 | 0.47 | 0.24 | 0.16 | 0 | 0 | 0 | 0 |
| 2 Months 104° F. | 0.62 | 0.62 | 0.20 | 0.18 | 0 | 0 | 0 | 0 |

The data tabulated above demonstrates that formulas according to the present invention (Exs. 1-4) are remarkably stable with regard to loss of oxygen as compared with dentifrice pastes prepared from bicarbonate, hydrogen peroxide mixtures. (Controls A-D).

EXAMPLES 5-6

Formulations of the present invention are further illustrates by examples of Table III.

TABLE III

Further Examples of Tooth Powder Formulations Containing Sodium Bicarbonate And A Hydrogen Peroxide Releasing Agent

| Example 5 | |
|---|---|
| Sodium Percarbonate | 4.0 |
| Sodium Saccharin | 1.5 |
| Spray Dried Flavor (20% Active Oil) | 2.0 |
| Sodium Fluoride | 0.22 |
| Magnesium Oxide | 0.1 |
| Sodium Bicarbonate | 92.18 |
| | 100.00 |

| Example 6 | |
|---|---|
| Sodium Percarbonate | 6.0 |
| Sodium Saccharin | 0.7 |
| Spray Dried Flavor (20% Active Oil) | 1.0 |
| Sodium Monofluorophosphate | 0.76 |
| Magnesium Oxide | 0.10 |
| Dicalcium Phosphate | 20.00 |
| Sodium Bicarbonate | 71.44 |
| | 100.00 |

EXAMPLE 7

A comparison was made between the stability of tooth powders containing sodium percarbonate (Example 7), urea peroxide (Controls E-F), and urea peroxide-based tooth powders containing anhydrous sodium acetate as a stabilizer (Controls G-H).

The tooth powders were prepared according to the formualos of Table IV:

TABLE IV

Compositions Of Urea Peroxide Tooth Powder Controls In Comparison With A Composition Of The Present Invention

| | Example 7 | Control E | Control F |
|---|---|---|---|
| Sodium Bicarbonate (Median Particle Size 74-149 Microns) | 86.18 | 86.18 | 87.68 |
| Sodium Fluoride | 0.22 | 0.22 | 0.22 |
| Urea Peroxide | — | 10.0 | 8.5 |
| Sodium Percarbonate | 10.0 | — | — |
| Saccharin | 2.0 | 1.5 | 1.5 |
| Flavor | 1.5 | 2.0 | 2.0 |
| Magnesium Oxide | 0.1 | 0.1 | 0.1 |
| | 100.0 | 100.0 | 100.0 |

| | Control G | Control H |
|---|---|---|
| Sodium Bicarbonate | 81.18 | 82.68 |
| Sodium Fluoride | 0.22 | 0.22 |
| Urea Peroxide | 10.0 | 8.5 |
| Flavor | 2.0 | 2.0 |
| Saccharin | 1.5 | 1.5 |
| MgO | 0.1 | 0.1 |
| Anhydrous Sodium Acetate | 5.0 | 5.0 |
| | 100.0 | 100.0 |

The above products were filled into plastic 4 oz. sealed powder dispensing containers. Two samples of each formulation were stored at room temperature and a third was stored at 40° C.

The results are as shown in Table V:

TABLE V

Comparison Of The Stability Of A Composition Of The Present Invention (Example 7) With The Stability Of Tooth Powders Containing Urea Peroxide

| | Example 7 | E | F | G | H |
|---|---|---|---|---|---|
| Room Temp-2 days | * | ** | ** | — | — |
| Room Temp-10 days | — | — | — | 0.24% $O_2$ | 0.49% $O_2$ |
| 40° C. - 2 days | * | * | * | — | — |
| 40° C. - 4 days | — | — | — | 0% $O_2$ | 0% $O_2$ |
| 40° C. - 10 days | — | 0% $O_2$ | 0% $O_2$ | — | — |
| 40° C. - 17 days | 1.05% $O_2$ | — | — | — | — |

*No visible signs of $O_2$ release; package did not appear to be under pressure.
**Visible decomposition; package visibly expanded in size due to pressure build up in the package.

The results illustrate the greater stability of sodium bicarbonate/sodium percarbonate tooth powder dentifrices in comparison to tooth powder dentifrice compositions prepared with urea peroxide.

Contrasting Dentifrices Containing Urea Peroxide As The Hydrogen Peroxide-Releasing Agent Tests were run to determine the stability of toothpastes prepared according to Gordon, U.S. Pat. No. 4,522,805, see Tables VI and VII (Controls I-K).

TABLE VI

Toothpaste Compositions Containing Urea Peroxide

|  | Control I | Control J | Control K |
|---|---|---|---|
| Sodium Bicarbonate[1] | 15.0 | 25.0 | 23.5 |
| Calcium Carbonate | 8.0 | 15.0 | 8.0 |
| Urea Peroxide | 8.5 | 10.0 | — |
| Acidulated Sodium Fluoride[2] | 0.5 | 0.75 | 0.5 |
| Paste Carrier[3] | 68.0 | 49.25 | 68.0 |

[1]The mean particle size of the sodium bicarbonate crystals used was between 74 and 149 microns. However, the particle size of the sodium bicarbonate used would not affect the stability of the toothpaste formulation.
[2]Acidulated sodium fluoride consisted of 1.8% sodium fluoride and 0.2% phosphoric acid in aqueous solution.
[3]The Paste Carrier contained, as a % of the complete formula:

|  | Control I | Control J | Control K |
|---|---|---|---|
| Sorbitol | 20.2 | 14.6 | 20.2 |
| Sodium Lauryl Sulfate | 1.7 | 1.2 | 1.7 |
| Glycerol | 11.0 | 8.0 | 11.0 |
| Water | 32.4 | 23.5 | 32.4 |
| CMC | 0.9 | 0.65 | 0.9 |
| Flavor | 1.0 | 0.7 | 1.0 |
| Sweetener (Saccharin) | 0.2 | 0.2 | 0.2 |
| Preservative (Sodium Benzoate) | 0.6 | 0.4 | 0.6 |
|  | 100.0 | 100.0 | 100.0 |

Controls formulas I-K were prepared and filled into three sealed toothpaste tubes. Two tubes of each product were aged at room temperature and one tube of each product was aged at 40° C. The results are shown in Table VII:

TABLE VII

Stability Data Of Toothpastes Containing Urea Peroxide As A Hydrogen Peroxide Releasing Agent

|  | Controls |  |  |
|---|---|---|---|
|  | I | J | K |
| Room temp. 24 hrs. | tubes burst[1] | tubes burst[1] | not gassed[2] |
| Room temp. one month | — | — | not gassed[2] |
| 40° C. - 24 hours | tubes burst[1] | tubes burst[1] | not gassed[2] |
| 40° C. - one month | — | — | gassed a small amount[3] |

[1]Sufficient pressure built up that the bottom of the sealed tubes blew open.
[2]The tubes remained intact.
[3]The tube expanded but did not burst open.

The results illustrated in Table VII clearly show the instability of urea peroxide in toothpastes prepared according to Gordon, U.S. Pat. No. 4,522,805 (Controls I-J). Additionally, toothpastes prepared according to Gordon, U.S. Pat. No. 4,522,805 but not containing urea peroxide are only marginally stable (Control K).

The preceding disclosure should be construed as illustrative only. The scope of the invention should be interpreted in accordance with the following claims:

We claim:

1. A tooth powder, comprising at least 40% by weight of a mixture of sodium bicarbonate and sodium percarbonate, the percarbonate being present in an amount sufficient to release from 0.5 to 5% hydrogen peroxide by weight of the tooth powder, upon contact with water.

2. The tooth powder of claim 1, wherein the sodium bicarbonate is incorporated in an amount of from 50 to 98% of the tooth powder, in the form of particles having a median particle size within the range of 74–210 microns.

3. The tooth powder of claim 1, wherein the sodium percarbonate is present in an amount of from 1 to 12% by weight of the tooth powder.

4. The tooth powder of claim 1, further comprising from 0.2 to 2% by weight of a fluoridating agent.

5. The tooth powder of claim 1, further comprising from 0.1 to 5% of a sweetener.

6. The tooth powder of claim 1, further comprising from 0.2 to 3.0% by weight of a flavoring agent.

7. The tooth powder of claim 1, further comprising from 1 to 50% by weight of a secondary abrasive.

8. The tooth powder of claim 1, further comprising up to 1% by weight of a flow aid.

9. The tooth powder of claim 1, comprising:

| sodium bicarbonate | 48 to 98% |
|---|---|
| sodium percarbonate | 1 to 12% |
| fluoridating agent | 0.2 to 2% |
| flavoring agent | 0.2 to 3% |
| sweetener | 0.1 to 5 |
| secondary abrasive | 0 to 50% |
| surfactant | 0 to 3% |

10. The tooth powder of claim 1, comprising:

| sodium bicarbonate | 89 to 94% |
|---|---|
| sodium percarbonate | 4 to 6% |
| flavoring agent | 1 to 2% |
| sweetener | 1 to 2% |
| flow aid | 0 to 1% |

11. A method of cleaning the teeth and gums, comprising applying a tooth powder to the teeth and gums, said tooth powder comprising at least 40% by weight of a mixture of sodium bicarbonate and sodium percarbonate, the percarbonate being present in an amount sufficient to release from 0.5 to 5% hydrogen peroxide by weight of the tooth powder, upon contact with water.

12. The method of claim 9, wherein the sodium bicarbonate is incorporated in an amount of from 50 to 98% of the tooth powder, in the form of particles having a median particle size within the range of 74 to 210 microns.

13. The method of claim 9, wherein the sodium percarbonate is present in an amount of from 1 to 12% by weight of the tooth powder.

14. The method of claim 9, wherein the tooth powder further comprises from 0.2 to 2% by weight of a fluoridating agent.

15. The method of claim 9, wherein the tooth powder further comprises from 0.1 to 5% of a sweetener.

16. The method of claim 9, wherein the tooth powder further comprises from 0.20 to 3.0% by weight of a flavoring agent.

17. The method of claim 9, wherein the tooth powder further comprises from 1 to 50% by weight of a secondary abrasive.

18. The method of claim 9, wherein the tooth powder further comprises from 0.1 to 0.2% by weight of a flow aid.

19. The method of claim 9, wherein the tooth powder comprises:

| sodium bicarbonate | 48 to 98% |
|---|---|
| sodium percarbonate | 1 to 12% |
| fluoridating agent | 0.2 to 2% |
| flavoring agent | 0.2 to 3% |
| sweetener | 0.1 to 5% |

| | |
|---|---|
| -continued | |
| secondary abrasive | 0 to 50% |
| surfactant | 0 to 3% |

20. The method of claim 9, wherein the tooth powder comprises:

| | |
|---|---|
| sodium bicarbonate | 89 to 94% |
| sodium percarbonate | 4 to 6% |
| flavoring agent | 1 to 2% |
| sweetener | 1 to 2% |
| flow aid | 0 to 1% |

* * * * *